US007504530B2

(12) United States Patent
Sodervall et al.

(10) Patent No.: US 7,504,530 B2
(45) Date of Patent: Mar. 17, 2009

(54) METHODS FOR THE PREPARATION OF FISPEMIFENE FROM OSPEMIFENE

(75) Inventors: Marja Sodervall, Oulu (FI); Maire Eloranta, Oulu (FI); Arja Kalapudas, Oulu (FI); Brian Kearton, Nottingham (GB); Michael McKenzie, Leicester (GB)

(73) Assignee: Hormos Medical Ltd., Turku (FI)

( * ) Notice: Subject to any disclaimer, the term of this patent is extended or adjusted under 35 U.S.C. 154(b) by 0 days.

(21) Appl. No.: 12/030,415

(22) Filed: Feb. 13, 2008

(65) Prior Publication Data

US 2008/0214860 A1 Sep. 4, 2008

Related U.S. Application Data

(60) Provisional application No. 60/889,835, filed on Feb. 14, 2007.

(51) Int. Cl.
C07C 39/12 (2006.01)
C07C 69/76 (2006.01)

(52) U.S. Cl. .......................... 560/60; 560/55; 568/731; 568/744; 568/745

(58) Field of Classification Search .................. None
See application file for complete search history.

(56) References Cited

U.S. PATENT DOCUMENTS

| 4,117,121 | A | 9/1978 | Gallo-Torres |
| 4,656,187 | A | 4/1987 | Black et al. |
| 4,696,949 | A | 9/1987 | Toivola et al. |
| 4,894,373 | A | 1/1990 | Young |
| 4,935,243 | A | 6/1990 | Borkan et al. |
| 4,996,225 | A | 2/1991 | Toivola et al. |
| 5,118,667 | A | 6/1992 | Adams et al. |
| 5,189,212 | A | 2/1993 | Ruenitz |
| 5,192,525 | A | 3/1993 | Yang et al. |
| 5,196,435 | A | 3/1993 | Clemens et al. |
| 5,352,699 | A | 10/1994 | Jackson |
| 5,446,203 | A | 8/1995 | McNelis |
| 5,470,883 | A | 11/1995 | Stromberg |
| 5,491,173 | A | 2/1996 | Toivola et al. |
| 5,567,714 | A | 10/1996 | Bruns |
| 5,658,931 | A | 8/1997 | Bryant et al. |
| 5,691,355 | A | 11/1997 | Bryant et al. |
| 5,693,674 | A | 12/1997 | Bitoniti |
| 5,719,136 | A | 2/1998 | Chwalisz et al. |
| 5,747,059 | A | 5/1998 | Korsgaard et al. |
| 5,750,576 | A | 5/1998 | DeGregorio et al. |
| 5,807,899 | A | 9/1998 | Bohlmann et al. |
| 5,821,254 | A | 10/1998 | Sporn et al. |
| 5,827,892 | A | 10/1998 | Loser et al. |
| 5,852,059 | A | 12/1998 | Thompson |
| 5,877,219 | A | 3/1999 | Willson |
| 5,912,273 | A | 6/1999 | DeGregorio et al. |
| 6,037,379 | A | 3/2000 | Harkonen et al. |
| 6,245,352 | B1 | 6/2001 | Arbuthnot et al. |
| 6,245,819 | B1 | 6/2001 | Halonen et al. |
| 6,395,785 | B1 * | 5/2002 | Sodervall et al. ............ 514/571 |
| 6,525,084 | B2 | 2/2003 | Rasmussen et al. |
| 6,576,645 | B1 * | 6/2003 | Sodervall et al. ............ 514/317 |
| 6,632,447 | B1 | 10/2003 | Steiner et al. |
| 6,875,775 | B2 * | 4/2005 | Sodervall et al. ............ 514/317 |
| 6,891,070 | B2 * | 5/2005 | Kalapudas et al. .......... 568/609 |
| 6,984,665 | B2 | 1/2006 | Blom et al. |
| 2001/0034340 | A1 | 10/2001 | Pickar |
| 2004/0248989 | A1 | 12/2004 | Santti et al. |
| 2005/0182143 | A1 | 8/2005 | Anttila |
| 2005/0187302 | A1 | 8/2005 | Blom |
| 2005/0215528 | A1 | 9/2005 | Furuya et al. |
| 2007/0104742 | A1 | 5/2007 | Lehtola et al. |
| 2007/0197664 | A1 | 8/2007 | Steiner et al. |
| 2007/0203180 | A1 | 8/2007 | Hoekstra et al. |

FOREIGN PATENT DOCUMENTS

| EP | 0 095 875 A3 | 12/1983 |
| EP | 0 664 124 A1 | 7/1995 |
| EP | 0 779 808 B1 | 8/1999 |
| EP | 0 760 651 B1 | 7/2001 |
| EP | 1 125 582 A2 | 8/2001 |
| WO | WO 92/06068 A1 | 4/1992 |
| WO | WO 93/19746 A1 | 10/1993 |
| WO | WO 95/26720 A1 | 10/1995 |
| WO | 199607402 * | 3/1996 |
| WO | WO 96/07402 A1 | 3/1996 |
| WO | WO 96/35417 A1 | 11/1996 |
| WO | WO 96/40616 A1 | 12/1996 |
| WO | WO 97/32574 A1 | 9/1997 |
| WO | WO 99/42427 A1 | 8/1999 |
| WO | WO 99/63974 A2 | 12/1999 |
| WO | WO 01/36360 A1 | 5/2001 |
| WO | WP 01/54699 A1 | 8/2001 |
| WO | WO 02/07718 A1 | 1/2002 |
| WO | WO 02/090305 A1 | 11/2002 |
| WO | WO 03/047504 A2 | 6/2003 |
| WO | WO 03/103649 A1 | 12/2003 |
| WO | WO 2005/079777 A1 | 9/2005 |

OTHER PUBLICATIONS

U.S. Appl. No. 12/030,420, filed Feb. 13, 2008, Marja Soderall et al.
B.H. Mitlak et al., "Selective Estrogen Receptor Modulators," Drugs 57(5):653-663, May 1999.
Budavari, S. et al., eds., The Merck Index, Eleventh Edition, p. 1430, No. 9019, Merck & Co., Inc., Rathway, NJ, USA (1989).
Dimaraki et al. (European Journal of Endocrinology, vol. 150, pp. 481-487; 2004).
Ferguson et al., Alkali Metal Ion Mediated Cyclization of 4,4'-(3,6-dioxaocta-1,8-diyloxy)-bis(benzophenone), Tetrahedron Letters, Jun. 1993, vol. 34, No. 23, pp. 3719-3722.

(Continued)

Primary Examiner—Karl J Puttlitz
(74) Attorney, Agent, or Firm—Brinks Hofer Gilson & Lione

(57) ABSTRACT

The present invention concerns a method for preparation of fispemifene by use of ospemifene as a starting material.

14 Claims, No Drawings

OTHER PUBLICATIONS

G.K. Bolhuis, K. Zuurman, G.H.P. te Wierik; Improvement of dissolution of poorly soluble drugs by solid deposition on a super disintegrant. II. The choice of super disintegrants and effect of granulation; European Journal of Pharmaceutical Sciences; 1997; 63-69; Elsevier Science B.V.

Goldstein, S.R. et al.; "A pharmacological review of selective oestrogen receptor modulators," Human Reproduction Udate 6:212-224, Oxford university Press (May-Jun. 2000).

Grodstein, F. and Stampfer, M.J., "Estrogen for women at varying risk of coronary disease," Maturitas 30:19-26, Elsevier Science Ireland Ltd. (1998).

Henderson, V.W., "Estrogen, Cognition, and a Woman's Risk of Alzheimer's Disease," The American Journal of Medicine 103:11S-18S, Excerpta Medica, Inc. (1997).

International Search Report for International Application No. PCT/FI00/00946, mailed Feb. 8, 2001.

Jordan, V. Craig; "Antiestrogens and Selective Estrogen Receptor Modulators as Multifunctional Medicines, 2. Clinical Considerations and New Agents," Journal of Medicinal Chemistry, Vo. 46, No. 7, Mar. 27, 2003, pp. 1081-1111.

K.C. Baynes et al., "Selective oestrogen receptor modulators: a new paradigm for HRT," Curr. Opin Obstet Gynecol 10(3): 189-192, Jun. 1998.

Kangas, L. et al., "A new triphenylethylene compound, Fc-1157a: II. Antitumor effects," Cancer Chemother. Pharmacol. 17:109-113, Springer-Verlag (1986).

Kangas, L. et al., "Bioluminescence of Cellular ATP: A New Method for Evaluating Cytotoxic Agents In Vitro," Medical Biology 62:338-343, Duodecim (1984).

Kangas, L., "Biochemical and pharmacological effects of toremifene metabolities," Cancer Chemother. Pharmacol. 27:8-12, Springer-Verlag (Apr. 1990).

Kauffman, Raymond F., et al., "Selective Estrogen Receptor Modulators," Drug News & Perspectives 1995 8 (9) pp. 531-539.

Khovidhunkit, W. and Shoback, D.M., "Clinical Effects of Raloxifene Hydrochloride in Women," Ann. Intern. Med. 130:431-439, American College of Physicians (Mar. 1999). Lobo, R.A., "Benefits and risks of estrogen replacement therapy," Am. J. Obstet. Gynecol. 173:982-989, Mosby-Year Book, Inc. (1995).

Lobo, R.A., "Benefits and risks of estogren replacement therapy," Am. J. Obstet. Gynecol. 173:982-989, Mosby-Year Book, Inc. (1995).

M. Whitehead, "Treatments for menopausal and post-menopausal problems: present and future," Baillieres Clin Obstet Gynaecol 10(3): 515-530, Sep. 1996 (online abstract).

M.M. Kennedy "Tamoxifen and the endometrium: review of 102 cases and comparison with HRT-related-and non-HRT-related endometrial pathology," Int J Gynecol Pathol 18(2): 130-137, Apr. 1999 (online abstract).

M.W. DeGregorio et al., "Hormone replacement therapy and breast cancer: revisiting the issues," J AM Pharm Assoc. 38(6): 738-744, Nov.-Dec. 1998, (online abstract).

Macgregor, J.I. and Jordan, V.C., "Basic Guide to the Mechanisms of Antiestrogen Action," Pharmacol. Rev. 50:151-196, Williams and Wilkins Co. (1998).

Merriam-Webster's Medical Dictionary (c) [online], Merriam-Webster, Inc., 2002 [retrieved on May 20, 2008]. Retrieved from the Internet: <URL: http://dictionary.reference.com/browse/therapeutic>.

Odeku Oluwatoyin A., Fell, John T.; Effects of the method of preparation on the compression, mechanical, and release properties of Khaya gum matrices; Pharmaceutical development and technology; 2006; vol. 11; 435-436.

Peng, Z. et al., "The Mechanical Strength of Bone in Different Rat Models of Experimental Osteoporosis," Bone 15:523-532, Elsevier Science Ltd. (1994).

Plouffe, L., "Selective Estrogen Receptor Modulators (SERMs) in Clinical Practice," J. Soc. Gynecol. Investig. 7:S38-S46, Elsevier Science Inc. (Jan. -Feb. 2000).

Porter, Christopher J. H., et al., "Lipid Based Formulations for Oral Administration," Journal of Receptor & Signal Transduction Research, 21 (2&3) 215-257 (2001).

Qu, Q. et al., "Selective Estrogenic Effects of a Novel Triphenylethylene Compounds, FC1271a, on Bone, Cholesterol Level, and Reproductive Tissues in Intact and Ovariectomized Rats," Endocrinology 141: 809-820, Association of the Sutudy of Internal Secretions (Feb. 2000).

Quinton Singh, Hiren Patel, Mohamed Cassim; Comparative Evaluations of Tablet Formulations; Rhodes University, School of Pharmaceutical Sciences, Department of Pharmaceutics, Rhodes University, Grahamstown, 6140, RSA; www.ru.ac.za/academic/departments/pharmacy/jrats/vol1_1/poster6/tablet8.html; printed Dec. 3, 2007; 1-6.

Rudnic, E.M., "Oral Solid Dosage Forms", Remington: The Science and Practice of Parmacy, Gennaro, A.R., editor, 20$^{th}$ Ed. Chapter 45, pp. 858-871.

S.K. Voipio, et al., "Effects of ospemifene (FC-1271a) on uterine endometrium, vaginal maturation index, and hormonal status in healthy postmenopausal women." Maturitas vol. 43, 207-214 (2002).

Salvolainen-Peltonen et al.; "Selective Estrogen Receptor Modulators Prevent Neointima Formation After Vascular Injury"; Molecular and Cellular Endocrinology, vol. 227, 2004, pp. 9-20.

Simberg, N.H. et al, "In Vitro and In Vivo Binding of Toremifene and Its Metabolites in Rat Uterus," Steroid Biochem. vol. 36: 197-202, Pergamon Press plc (1990).

SJ Laight, PCM Mossop, MC Wilkinson; Comparative evaluation of two aspirin formulation techniques; www.ru.ac.za/academic/departments/pharmacy/jrats/vol1_1/poster5/tablet2.html; printed Dec. 3, 2007; 1-6.

Terenius, L., "Structure-Activity Relationships of Anti-Ostrogens With Regard to Interaction With 17β-Oestradiol in the Mouse Uterus and Vargina," Acta Endocrinol. 66:431-447, Scandinavian University Press (1971).

The American Heritage © Science Dictionary [online], Houghton Mifflin Company, 2002 [retrieved on May 20, 2008]. Retrieved from the Internet:-URL: http://dictionary.reference.com/browse/metabolite>.

* cited by examiner

METHODS FOR THE PREPARATION OF FISPEMIFENE FROM OSPEMIFENE

CROSS REFERENCE TO RELATED APPLICATIONS

This application claims priority to U.S. Patent Provisional Patent Application No. 60/889,835 filed Feb. 14, 2007, hereby incorporated by reference.

BACKGROUND

1. Field of the Invention

This invention relates to the preparation of fispemifene using ospemifene as a starting material.

2. Description of Related Art

The publications and other materials used herein to illuminate the background of the invention, and in particular, cases to provide additional details respecting the practice, are incorporated by reference.

Ospemifene, (Z)-2-[4-(4-Chloro-1,2-diphenyl-but-1-enyl) phenoxy]ethanol, which is one of the main metabolites of toremifene, is known as an estrogen agonist and antagonist (Kangas, Cancer Chemother. Pharmacol. (1990) 27:8-12; WO 96/07402 and WO 97/32574). Ospemifene has relatively weak estrogenic and antiestrogenic effects in the classical hormonal tests (Kangas, 1990). It has anti-osteoporosis actions and it decreases total and LDL cholesterol levels in both experimental models and in human volunteers. It also has antitumor activity in an early stage of breast cancer development in an animal breast cancer model. Ospemifene is also the first SERM (selective estrogen receptor modulator) which has been shown to have beneficial effects in climacteric syndromes in healthy women. The use of ospemifene for the treatment of certain climacteric disorders and atrophy-related diseases or disorders in postmenopausal women is disclosed in WO 02/07718 and WO 03/103649.

WO 01/36360 describes a group of SERMs, which are tissue-specific estrogens and which can be used in women in the treatment of climacteric symptoms, osteoporosis, Alzheimer's disease and/or cardiovascular diseases without the carcinogenic risk. Certain compounds can be given to men to protect them against osteoporosis, cardiovascular diseases and Alzheimer's disease without estrogenic adverse events (gynecomastia, decreased libido etc.). Of the compounds described in said patent publication, the compound (Z)-2-{2-[4-(4-chloro-1,2-diphenylbut-1-enyl)phenoxy]ethoxy}ethanol (also known under the generic name fispemifene) has shown a very interesting hormonal profile suggesting that it will be especially valuable for treating disorders in men. WO 2004/108645 and WO 2006/024689 suggest the use of fispemifene for treatment or prevention of age-related symptoms in men, such as lower urinary tract symptoms and diseases or disorders related to androgen deficiency in men.

Known methods for the syntheses of compounds like ospemifene and fispemifene include rather many steps. WO 02/090305 describes a method for the preparation of fispemifene, where, in a first step, a triphenylbutane compound with a dihydroxysubstituted butane chain is obtained. This compound is in a second step converted to a triphenylbutene where the chain is 4-chlorosubstituted. Then the desired Z-isomer is crystallized. Finally, the protecting group is removed to release the ethanol-ethoxy chain of the molecule.

SUMMARY

Both ospemifene and fispemifene are likely to be commercialized in the near future. Thus, there is a great need for powerful methods for the preparation of these compounds in large scale. Particularly, the object of this invention is to provide a method for synthesis of fispemifene using ospemifene as starting material in only two steps, with no need to purify the intermediate.

Thus, according to one aspect, this invention concerns a method for the preparation of a compound of formula (I)

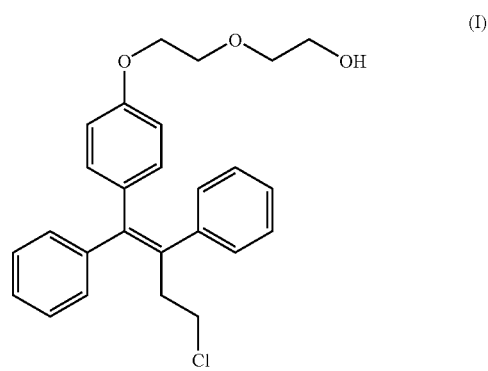

wherein a compound of formula (II)

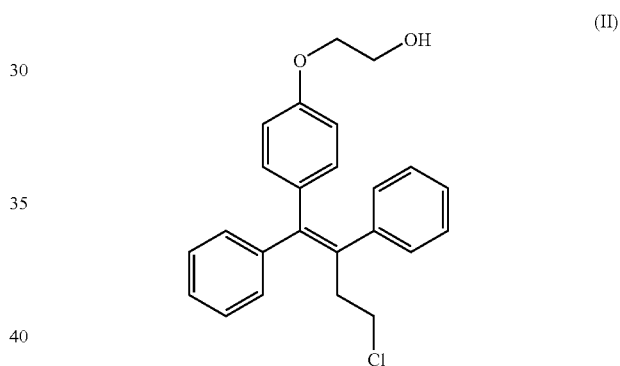

is alkylated with an alkylating reagent of the formula Hal-$CH_2$—COOR, wherein Hal is halogen and R is an alkyl, to give a compound of formula (III)

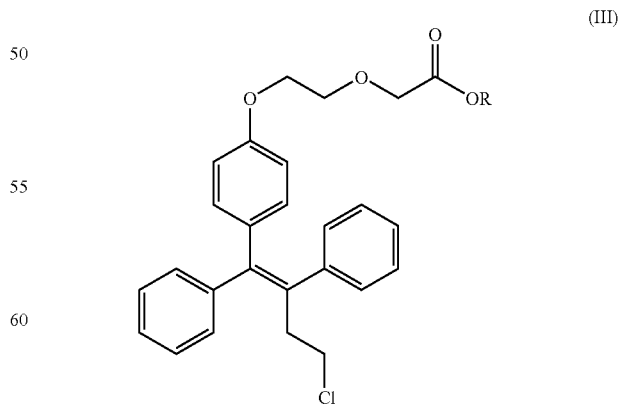

and the ester of formula (III) is reduced to give the compound of formula (I).

This invention is also directed to a group of novel compounds of formula (III) where R is a $C_1$-$C_4$-alkyl, preferably methyl, ethyl or t-butyl.

Furthermore, this invention concerns the use of compounds of formula (III) in the manufacture of fispemifene.

DETAILED DESCRIPTION

Fispemifene is the Z-isomer of the compound of formula (I)

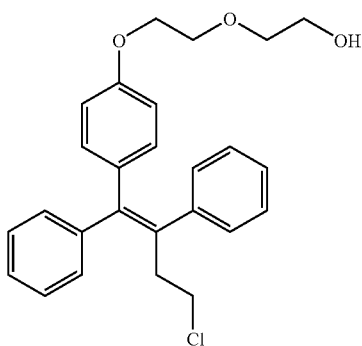

(I)

The starting material, compound (II), may be prepared by methods known to those of ordinary skill in the art. The alkylating agent is Hal-$CH_2$—COOR. The alkyl R in the alkylating reagent is preferably a $C_{1-4}$-alkyl, most preferably ethyl. Examples of a $C_{1-4}$-alkyl also include methyl, propyl, isopropyl, n-butyl, sec-butyl, isobutyl, and t-butyl. The step of alkylating is conducted at a temperature and for a time sufficient to achieve substantial alkylation of compound (II). The halogen (Hal) in the alkylating reagent is preferably I, Br or Cl, and most preferably Br.

The reduction of the compound (III) to compound (I) is preferably carried out by lithium aluminium hydride, although other reducing agents well known to those of ordinary skill in the art may also be used. The step of reduction is carried out at a temperature and for a time sufficient to produce substantially pure fispemifene.

The invention will be illuminated by the following non-restrictive Examples.

EXAMPLE 1

{2-[4-(4-Chloro-1,2-diphenyl-but-1-enyl)-phenoxy]-ethoxy}-acetic acid ethyl ester (Compound III)

2-[4-(4-Chloro-1,2-diphenyl-but-1-enyl)-phenoxy]-ethanol (Compound II) (0.3 g, 0.79 mmol) was dissolved in tetrahydrofuran (5 ml) under a nitrogen atmosphere. Sodium hydride (0.058 g, 1.21 mmol) was added in THF (5 ml) to the solution and the mixture was stirred at room temperature for an hour. Then the mixture was cooled to 0° C., ethyl bromo acetate (0.4 g, 2.38 mmol) was added and the stirring was continued for 5 hours at 0-5° C. The mixture was allowed to warm up to room temperature and stirring was continued overnight. Then the reaction is quenched with water and ethyl acetate. The aqueous layer was separated and extracted with ethyl acetate. The organic phase was washed with water, dried with sodium sulphate and evaporated to dryness. The residue was used in the next reaction step without further purification.

$^1$H NMR (200 MHz, $CDCl_3$): 1.25 (t, 3H, $CH_2\underline{CH_3}$), 2.94 (t, 2H, =$\underline{CH_2}CH_2Cl$), 3.44 (t, 2H, =$CH_2\underline{CH_2}Cl$), 3.85-3.90 (m, 2H, $OCH_2\underline{CH_2}O$ $CH_2CO$), 4.03-4.07 (m, 2H, O$\underline{CH_2}CH_2OCH_2CO$), 4.18 (s, 2H, $OCH_2CH_2O\underline{CH_2}CO$), 4.19 (q, 2H, $\underline{CH_2}CH_3$), 6.58 (d, 2H, aromatic proton ortho to oxygen), 6.80 (d, 2H, aromatic proton meta to oxygen), 7.1-7.43 (m, 10H, aromatic protons).

EXAMPLE 2

2-{2-[4-(4-Chloro-1,2-diphenyl-but-1-enyl)-phenoxy]-ethoxy}-ethanol (Compound I)

{2-[4-(4-Chloro-1,2-diphenyl-but-1-enyl)-phenoxy]-ethoxy}-acetic acid ethyl ester was dissolved in tetrahydrofuran at room temperature under nitrogen atmosphere. Lithium aluminium hydride was added to the solution in small portions until the reduction reaction was complete. The reaction was quenched with saturated aqueous ammonium chloride solution. The product was extracted into toluene, which was dried and evaporated in vacuo. The residue was purified with flash chromatography with toluene/triethyl amine (9.5:0.5) as eluent. Yield 68%.

$^1$H NMR (200 MHz, $CDCl_3$): 2.92 (t, 2H, =$\underline{CH_2}CH_2Cl$), 3.42 (t, 2H, =$CH_2\underline{CH_2}Cl$), 3.59-3.64 (m, 2H, $OCH_2CH_2O$ $CH_2\underline{CH_2}OH$), 3.69-3.80 (m, 4H, $OCH_2\underline{CH_2}O\underline{CH_2}$ $CH_2OH$), 3.97-4.02 (m, 2H, $OCH_2CH_2OCH_2CH_2OH$), 6.57 (d, 2H, aromatic proton ortho to oxygen), 6.78 (d, 2H, aromatic proton meta to oxygen), 7.1-7.43 (m, 10H, aromatic protons).

It will be appreciated that the methods of the present invention can be incorporated in the form of a variety of embodiments, only a few of which are disclosed herein. It will be apparent for one of ordinary skill in the art that other embodiments exist and do not depart from the spirit of the invention. Thus, the described embodiments are illustrative and should not be construed as restrictive.

What is claimed is:

1. A method for the preparation of a compound of formula (I) comprising:

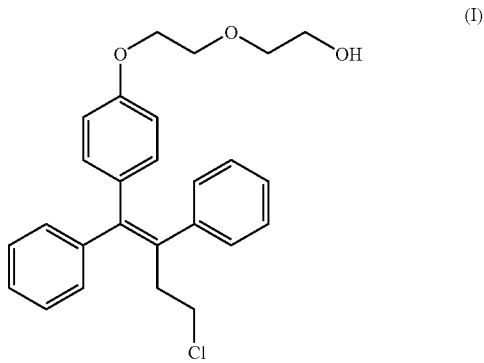

(I)

wherein a compound of formula (II)

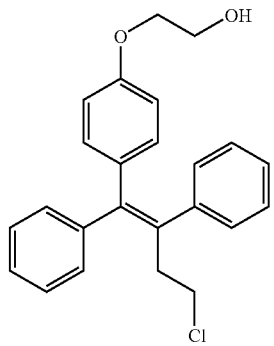

is alkylated with an alkylating reagent of the formula Hal-$CH_2$—COOR, wherein Hal is halogen and R is a $C_1$-$C_4$ alkyl, to give a compound of formula (III)

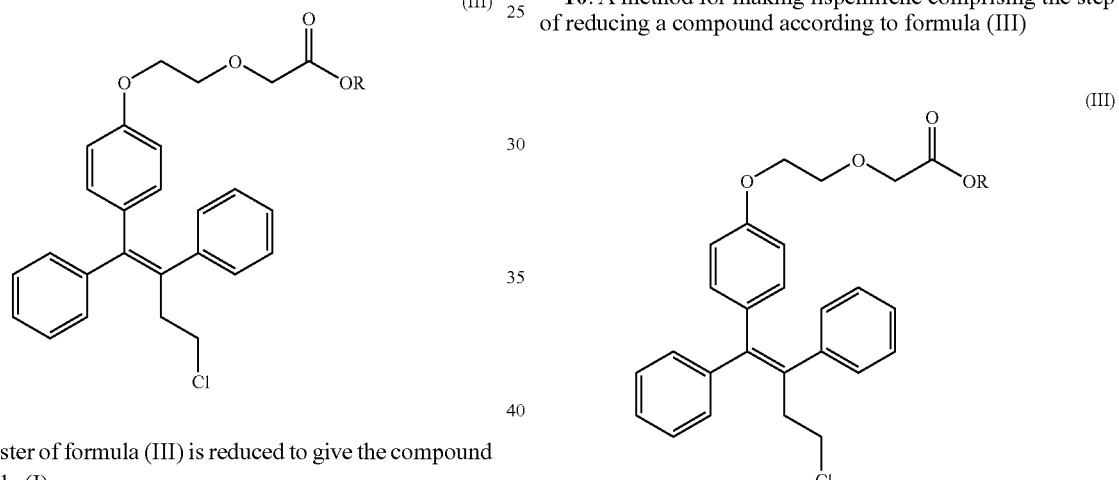

and the ester of formula (III) is reduced to give the compound of formula (I).

2. The method according to claim 1, wherein Hal is I, Br or Cl.

3. The method according to claim 2, wherein Hal is Br.

4. The method according to claim 1, wherein R is ethyl.

5. The method according to claim 1, wherein the reduction of the compound (III) is carried out by lithium aluminium hydride.

6. The method according to any of the foregoing claims, wherein the compound (I) is the Z-isomer.

7. A compound of formula (III)

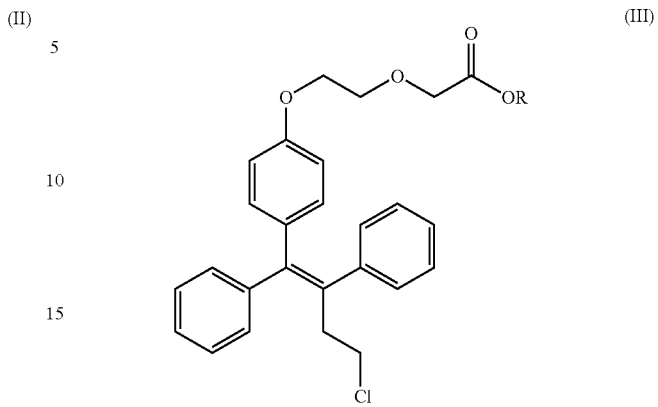

wherein R is a $C_{1-4}$-alkyl.

8. The compound according to claim 7 wherein R is methyl, ethyl, or t-butyl.

9. The compound according to claim 7 wherein R is ethyl.

10. A method for making fispemifene comprising the step of reducing a compound according to formula (III)

wherein R is $C_1$-$C_4$ alkyl, to make fispemifene.

11. The compound according to claim 10 wherein R is methyl, ethyl, or t-butyl.

12. The method according to claim 11, wherein R is ethyl.

13. The method according to claim 11, wherein the reduction of the compound (III) is carried out by lithium aluminium hydride.

14. The method according to any of the claims 10-13, wherein the compound (I) is the Z-isomer.

* * * * *